(12) United States Patent
Couderc et al.

(10) Patent No.: US 12,331,366 B2
(45) Date of Patent: Jun. 17, 2025

(54) PROCESS FOR TREATING LIGNOCELLULOSIC BIOMASS

(71) Applicant: IFP Energies nouvelles, Rueil-Malmaison (FR)

(72) Inventors: Sophie Couderc, Rueil-Malmaison (FR); Marc Jacquin, Rueil-Malmaison (FR); Caroline Aymard, Rueil-Malmaison (FR)

(73) Assignee: IFP Energies nouvelles, Rueil-Malmaison (FR)

( * ) Notice: Subject to any disclaimer, the term of this patent is extended or adjusted under 35 U.S.C. 154(b) by 0 days.

(21) Appl. No.: 17/707,030

(22) Filed: Mar. 29, 2022

(65) Prior Publication Data

US 2022/0325365 A1  Oct. 13, 2022

(30) Foreign Application Priority Data

Mar. 30, 2021 (FR) ..................... 2103229

(51) Int. Cl.
*C13B 10/14* (2011.01)
*C12P 7/10* (2006.01)

(52) U.S. Cl.
CPC ............. *C13B 10/14* (2013.01); *C12P 7/10* (2013.01)

(58) Field of Classification Search
CPC .... C13B 10/14; C12P 7/10; C12P 7/06; C12P 2201/00; C12P 19/12; C12P 19/14; C12P 19/02; C12P 19/00; Y02E 50/10; C13K 1/02; C13K 13/002
See application file for complete search history.

(56) References Cited

U.S. PATENT DOCUMENTS

| | | | | |
|---|---|---|---|---|
| 2,868,677 | A * | 1/1959 | Kopke | C13B 35/06 127/46.3 |
| 4,046,789 | A * | 9/1977 | Muller | C11B 13/00 426/417 |
| 8,067,193 | B2 * | 11/2011 | Hughes | C02F 1/56 426/11 |
| 10,077,283 | B2 * | 9/2018 | Dybov | C07G 1/00 |

FOREIGN PATENT DOCUMENTS

| | | | | |
|---|---|---|---|---|
| WO | WO 96/41052 | * 12/1999 | | D21C 3/20 |
| WO | 2008137639 A1 | 11/2008 | | |
| WO | 2018114905 A1 | 6/2018 | | |

OTHER PUBLICATIONS

Islam et al., Staged organosolv pretreatment to increase net energy and reactive lignin yield in whole oil palm tree biorefinery. Bioresource Technol., 2021, vol. 326, 124766, pp. 1-10. (Year: 2021).*
Qureshi et al., Application of Continuous Substrate Feeding to the ABE Fermentation: Relief of Product Inhibition Using Extraction, Perstraction, Stripping, and Pervaporation. Biotechnol. Prog., 1992, vol. 8: 382-390. (Year: 1992).*
Johansen et al., Influence of Extraction Solvent and Temperature on the Quantitative Determination of Oligosaccharides from Plant Materials by High-Performance Liquid Chromatography. J. Agric. Food. Chem., 1996, vol. 44: 1470-1474. (Year: 1996).*
Paramahans et al., Carbohydrate Corn position of the Millet Varagu. Starch/Starke, 1980, vol. 32(3): S. 73-76. (Year: 1980).*
Ostovareh et al., Efficient conversion of sweet sorghum stalks to biogas and ethanol using organosolv pretreatment Industrial Crops and Products, 2015, vol. 66: 170-177. (Year: 2015).*
Chen et al., Pretreatment efficiency and structural characterization of rice straw by an integrated process of dilute-acid and steam explosion for bioethanol production. Bioresource Technol., 2011, vol. 102: 2916-2924 (Year: 2011).*
Wang et al., Fractionation and characterization of lignin from steam-exploded corn stalk by sequential dissolution in ethanol-water solvent. Separation and Purification Technol., 2013, vol. 120: 402-409 (Year: 2013).*
Hongzhang et al: "Unpolluted fractionation of wheat straw by steam explosion and ethanol extraction", Bioresource Technology, Elsevier, Amsterdam, NL, vol. 98, No. 3, Feb. 1, 2007 (Feb. 1, 2007), pp. 666-676, XP005656281, ISSN: 0960-8524, DOI: 10.1016/J.BIORTECH.2006.02.029.
Wang Guanhua et al: "Fractionation and characterization of lignin from steam-exploded corn stalk by sequential dissolution in ethanol-water sol", Separation and Purification Technology, Elsevier Science, Amsterdam, NL, vol. 120, Oct. 28, 2013 (Oct. 28, 2013), pp. 402-409, XP028785353, ISSN: 1383-5866, DOI: 10.1016/J.SEPPUR.2013.10.029.
Panagiotopoulos I A et al: "A two-stage pretreatment approach to maximise sugar yield and enhance reactive ignin recovery from poplar wood chips", Bioresource Technology, Elsevier, Amsterdam, NL, vol. 130, Dec. 21, 2012 (Dec. 21, 2012), pp. 570-577, XP028980672, ISSN: 0960-8524, DOI: 10.1016/J.BIORTECH.2012.12.093.
Search report in corresponding FR application 2103229 dated Dec. 10, 2021 (pp. 1-3).

* cited by examiner

Primary Examiner — Ganapathirama Raghu
(74) Attorney, Agent, or Firm — Millen, White, Zelano & Branigan, P.C.; Brion P. Heaney (57) ABSTRACT

The present invention relates to a process for treating a lignocellulosic biomass pretreated beforehand (1), said process comprising the extraction of the free sugars from said pretreated biomass using an alcoholic or aqueous-alcoholic extraction solution (2), so as to obtain a liquid phase enriched in free sugars, called liquor (3), and a solid phase depleted in free sugars, called must (4).

23 Claims, 1 Drawing Sheet

PROCESS FOR TREATING LIGNOCELLULOSIC BIOMASS

TECHNICAL FIELD

The invention relates to a process for treating lignocellulosic biomass for producing "second-generation" (2G) sugary liquors. These sugary liquors may be used to produce other products via a chemical or biochemical/fermentation pathway (e.g. alcohols such as ethanol, butanol or other molecules, for example solvents such as acetone, furfural or xylitol, and other biobased molecules, etc.).

PRIOR ART

Lignocellulosic biomass represents one of the most abundant renewable resources on Earth. The substrates considered are very varied, and concern both ligneous substrates such as various woods (broad-leaved and coniferous), by-products derived from agriculture (wheat straw, rice straw, corn husks, bagasse, etc.) or else other papermaking, etc. industries. Lignocellulosic biomass is composed of three main polymers: cellulose (35% to 50%), which is a crystalline polysaccharide consisting essentially of glucose; hemicellulose (20% to 30%), which is an amorphous polysaccharide consisting mainly of xylose, galactose, arabinose, mannose, glucose; and of lignin (15% to 25%), which is a polymer of complex structure and of high molecular weight, composed of various phenolic monomers linked via ether bonds. These various polymers are responsible for the intrinsic properties of the plant wall and are organized in a complex entanglement. Among the three base polymers that make up lignocellulosic biomass, cellulose and hemicellulose are the ones that enable the production of "second-generation" (2G) sugary liquors and 2G ethanol. It should be noted that the composition of hemicelluloses can vary depending on the nature of the lignocellulosic biomass in question.

There are numerous processes for upgrading lignocellulosic biomass to 2G sugars or 2G ethanol, which differ in terms of the operating conditions applied and the nature of the reagents used to release the sugars. Nevertheless, the processes for upgrading lignocellulosic biomass to 2G sugars that have been the most developed on the industrial scale have in common notably a pretreatment step and a step of enzymatic hydrolysis by an enzymatic cocktail. The pretreatment step makes it possible to destructure the native biomass, and generally a part of the hemicellulose polymer is depolymerized in this step. The enzymatic hydrolysis targets mainly the cellulose, and the residual hemicelluloses; the polymers are depolymerized under the action of an enzyme cocktail.

These 2G sugary liquors can be used/upgraded for example in a fermentative or chemical process, as they are, or can optionally be subsequently treated. Usually, the overall process comprises intermediate separation steps and/or a step of purifying the final product(s).

The pretreatment makes it possible to modify the physicochemical properties of the lignocellulosic biomass so as to make the cellulose accessible to the enzymes and to achieve good reactivity in enzymatic hydrolysis. Many pretreatment techniques exist and allow establishment of the temperature of the biomass under varied chemical conditions. The pretreatment may be performed with or without addition of acidic or basic products. It may also be performed in a solvent such as water or an organic product, for instance alcohol ("organosolv" process), but also in a sparingly diluted medium such as steam. This pretreatment may also comprise a physical step such as defiberizing or explosive decompression in the context of a steam explosion. This pretreatment may also involve several steps for optimizing the overall process, for instance acidic cooking followed by a steam explosion or two consecutive steam explosions. The pretreatments hereinafter grouped together under the generic term "cooking" concern heat treatments, with temperatures greater than 100° C. For technological reasons, notably of mixing and pumpability, the cooking operations are carried out under conditions referred to as diluted, with cooking liquid/biomass mass ratios greater than 2. The cooking operations generally couple a heat effect with a chemical effect obtained by low or, on the contrary, high pH values and/or the use of solvents. This term "cooking" groups together for example acidic cooking, alkaline cooking, and "organosolv" cooking. The latter process involves pretreatment in the presence of one or more organic solvents and generally water. The solvent may be, in a non-limiting manner, an alcohol (ethanol), an acid such as acetic acid or formic acid, or else acetone. "Organosolv pulping" processes lead to at least partial dissolution of the lignin and partial dissolution of the hemicelluloses. There are thus two outlet streams: the pretreated substrate with residual cellulose, hemicellulose and lignin, and the solvent phase which contains a portion of the dissolved lignin and a portion of the hemicelluloses. There is generally a step of regeneration of the solvent, which makes it possible to extract a solid lignin stream. In certain pretreatments, termed "organosolv pulping" (notably with ethanol), the action of the organic solvent is improved by adding a strong acid (such as $H_2SO_4$). It is then also possible to envisage bringing the biomass into contact with the solvent via an impregnation reactor before the cooking phase and/or bringing the biomass into contact with the acid catalyst before performing "organosolv pulping" cooking.

A technological solution is well known to those skilled in the art for overcoming the technological problems of the cooking: Reactors which implement an explosive decompression as method for expelling the pretreated biomass (also called Steam gun or Steam explosion) make it possible to get around the problems of pumpability at the end of cooking. The pretreatment of steam explosion type makes it possible to work with liquid/biomass mass ratios of less than 2; the biomass is subjected to a proportionally small amount of steam. A portion of the steam used for the entrainment of the solid during the explosive decompression can subsequently be separated from the medium. The explosive decompression thus makes it possible to produce a pretreated must not containing continuous liquid phase; it can be described as "dry", as opposed to musts produced by conventional cooking operations, although its water content is generally greater than 30% by weight. Usually, steam explosion under acidic conditions is preferred, since it allows a good compromise between acidic hydrolysis of the hemicellulose and the reactivity of cellulose in enzymatic hydrolysis, with virtually total hydrolysis of the hemicellulose and a large improvement in the accessibility and reactivity of the cellulose to the enzymes. This pretreatment may be preceded by other treatment(s) (milling, impregnation, cooking, etc.).

It is noted that this type of pretreatment, cooking or steam explosion, requires a transformation of the raw biomass into a reactive pretreated substrate, before starting the subsequent steps for converting the cellulose, which is the most refractory polymer. After this pretreatment, sugars (C5 and C6 sugars) are released in water-soluble monomeric or oligomeric form. The extraction of these free sugars in a liquor is advantageous for upgrading in the rest of the process of biomass transformation or in another process (in parallel) or for marketing the sugary liquor per se. It is thus advantageous to extract these pretreated substrate free-sugar liquors, before the pretreated must in question, which will then be enriched in solid material and depleted of sugars, undergoes the subsequent cellulose conversion treatments. From this perspective, in the case of a pretreatment of cooking time, the liquid fraction and the solid fraction of the pretreated biomass are separated, and then the solid fraction is optionally washed with water in order to further recover sugars. On the other hand, in the case of a pretreatment of steam explosion type, a must with a high solids content (typically greater than 40% by weight) is recovered at the end of pretreatment. The extraction of the free sugars requires, beforehand, a step of "repulping" the must in water as described in patent EP-3 587 583, before separating the liquid fraction from the solid fraction, and then carrying out an optional washing of the solid fraction, with water, in order to further recover free sugars.

The cooking and/or steam explosion step is often preceded by an impregnation step. It is often followed by a step of enzymatic hydrolysis of the cellulose using a dedicated enzymatic cocktail. This enzymatic cocktail is a solution containing enzymes having cellulolytic and/or hemicellulolytic activities, which will selectively hydrolyse the cellulose polymer and optionally the residual hemicellulose polymers. Because the action of the enzymes is targeted, the residual lignin is barely affected by the enzymatic hydrolysis. The enzymatic hydrolysis is carried out under mild temperature and pH conditions. The temperature is typically from 30° C. to 55° C. and the pH is typically between 3 and 7. The reaction for enzymatic hydrolysis of the sugar polymers to monomers requires the addition of water molecules, the hydrolysis being promoted by the presence of a continuous liquid medium. There are many reactor technologies for implementing this. The enzymatic hydrolysis can be carried out directly on the pretreated biomass and/or on a pretreated biomass from which the soluble sugars have been extracted for example.

In certain cases, the step of enzymatic hydrolysis of the cellulose is followed by a step of fermentation, ethanolic fermentation for example, of the sugars released and a step of purification of the fermentation products. In certain configurations of the process scheme, the steps of enzymatic hydrolysis and of fermentation may take place in the same reactor, in a fermentation configuration known as SSF (Simultaneous Saccharification and Fermentation). When these two steps of the process are separated, such a scheme is referred to as being of the SHF type (Separated Hydrolysis and Fermentation). Examples are given in the document "Ethanol from lignocellulosics: A review of the economy", M. von Silvers and G. Zacchi, Bioresource Technology 56 (1996) 131-140.

It is then necessary to extract the free sugars present after the pretreatment step with a view to use in a subsequent step sensitive to the presence of solid, for example in the case of sensitivity of the fermentative microorganism used in a subsequent fermentation step, or in the case of recycling of the microorganism around this fermentation step or for facilitating the operation of purification and/or separation of the sugars or other fermentation products that could be obtained from these sugars. With this in mind, the liquid fraction and the solid fraction are separated. The solid fraction is in the form of a cake, in which a portion of the liquid fraction remains trapped by virtue of the limitations of the solid/liquid separation tools and the characteristics of the lignocellulosic biomass.

It is thus seen that at various steps in the biomass treatment processes, the products being treated are in the form of solid/liquid mixtures, and that it may be advantageous to extract at least a portion of the liquid phase from the solid phase in order to upgrade it and to optimize the overall process, and optionally carry out the washing of the solid phase so as to maximize the recovery of the soluble sugars.

Patent WO 2014/135755 proposes a process for treating biomass via the following succession of steps: a—a pretreatment step is performed by placing in contact and heating the biomass feedstock with water and an acidic or basic compound, so as to obtain a pretreated substrate, b—the pretreated substrate is placed in contact with cellulase enzymes and a liquid stream enriched in fermentation products obtained in step e) so as to obtain a hydrolysate including a solid residue and a liquid phase containing sugars, c—alcoholic fermentation of the hydrolysate is performed using an alcohol-forming microorganism so as to produce a fermentation wine including a solid material and a liquid phase containing fermentation products, d—at least a portion of the solid material contained in the fermentation wine is extracted so as to obtain a stream enriched in solid material and a fermentation wine depleted in solid material, e—the stream enriched in solid material is washed with a liquid stream so as to obtain said liquid stream enriched in fermentation products, the liquid stream enriched in fermentation products being recycled into step b), f—a step of separation of the fermentation wine depleted in solid material is performed so as to obtain at least one purified stream including an alcohol or a solvent and at least one stream of vinasse.

That patent thus proposes to perform the separation of lignin and of other possible inert solids after the fermentation step. The solid material predominantly composed of lignin is then subjected to washing with water to recover the trapped fermentation products, in particular the alcohols and the solvents. The liquid resulting from the washing is then recycled into the enzymatic hydrolysis unit, which may be the same unit as the fermentation unit or which may be different from the fermentation unit so as not to bring about dilution in the existing streams.

Patent EP 2 774 992 proposes to perform, in a process including a pretreatment step, a step of enzymatic hydrolysis and then a fermentation step, to extract at least a portion of the solid residue contained in the hydrolysate so as to obtain a stream of solid residue including lignin and a hydrolysate depleted in solid residue, and the stream of solid residue is then washed with a liquid stream such as water so as to recover a liquid phase enriched in sugars, which may be recycled into the enzymatic hydrolysis step to be able to upgrade the sugars without bringing about dilution of the streams in the process.

Patent EP 3 587 583 describes a process aimed at performing a two-step extraction of the free sugars on a pretreated biomass obtained by a pretreatment of steam explosion type: a first step, termed "repulping", which consists in bringing a dry must into contact with a mixing fluid by means of a mixer continuously, then a second step of extraction/washing carried out by a continuous filter, using a washing fluid in order to obtain a solid phase enriched in solid and depleted in free sugars and a plurality of liquid phases enriched in sugars, with at least partial recycling of a liquid phase extracted from the filter at the inlet of the mixer as mixing fluid. Partial recycling of another liquid phase extracted from the filter is carried out so that said liquid phase can be used as washing fluid.

These various biomass treatments therefore involve an extraction of the free sugars or of their products of fermentation of a biomass optionally already treated/converted at least partially in order to extract therefrom free sugars in a liquid phase that can be upgraded.

In order to increase the efficiency of this washing, which can also be expressed as the free sugar extraction yield, it is possible, at equal amounts of mixing water and of washing water, to increase the number of theoretical stages of the operation, and to adopt a countercurrent or crosscurrent operation mode, rather than a cocurrent operation mode. Moreover, an increase in the amount of washing (and/or mixing) water at equal configuration will result in an improvement in the extraction yield, but also in an increased dilution of the free sugars in the liquor extracted. However, in order to recover upgradable sugars from the liquor, operations for concentrating the liquor are usually carried out, notably by heating/evaporation, and the more dilute the liquor is, the greater the energy consumption in order to concentrate it.

An object of the invention is therefore to improve the manner in which an operation of extraction of the free sugars from lignocellulosic biomass after one or more treatments is carried out, notably while reducing the energy consumption/costs of the subsequent treatment/upgrading thereof.

SUMMARY OF THE INVENTION

A subject of the invention is first of all a process for treating a lignocellulosic biomass pretreated beforehand, said process comprising the extraction of the free sugars from said pretreated biomass using an alcoholic or aqueous-alcoholic extraction solution, so as to obtain a liquid phase enriched in free sugars, called liquor, and a solid phase depleted in free sugars, called must.

It has been demonstrated, with the invention, that carrying out the extraction of the free sugars from the pretreated lignocellulosic biomass using an alcoholic or aqueous-alcoholic solution would make it possible to reduce the costs associated with concentrating the extracted sugar liquors, this being without degrading the sugar extraction efficiency. However, this is an entirely surprising result, in so far as alcohols are rather poor solvents for sugars (solubility of sugars less than 1% by weight in the case of ethanol, which is moreover rather known for facilitating sugar crystallization, that is to say the complete opposite of what is desired in the context of the present invention).

Preferably, the alcoholic or aqueous-alcoholic solution used for the extraction according to the invention contains no compound other than alcohol (or a mixture of alcohols), and optionally water. It notably contains neither acid nor base nor an oxidizing agent.

The extraction of the free sugars according to the invention has also proved to be advantageous with regard to at least two other aspects:

Firstly, it has proved to be the case that the extraction, according to the invention, of the free sugars present in the solid/liquid mixture obtained after pretreatment of the lignocellulosic biomass makes it possible to improve the steps of purification of the sugars before their concentration. The pretreated lignocellulosic biomass generally in fact contains a not insignificant amount of mineral salts, and most particularly sulfate anions $SO_4^{2-}$ when the biomass has been pretreated with sulfuric acid. An effective means for eliminating them which is known to those skilled in the art is that of carrying out a liming step commonly performed on sugar liquors obtained from first-generation, 1G, biomass, that is to say the addition of a limewater containing calcium hydroxide. This treatment makes it possible to bring about the precipitation, inter alia, of the sulfate anions in the form of calcium sulfate. It has proved to be the case that carrying out liming on a sugar liquor obtained according to the invention with an extraction of the free sugars using an alcoholic or aqueous-alcoholic solution makes it possible to further eliminate sulfates, thus reducing the cost of the subsequent treatment operations.

Secondly, it proves to be the case that the biomass thus treated retains a (small) portion of the washing solution, therefore a (small) portion of alcohol according to the invention. In addition, the sugary liquors extracted also contain a certain proportion of alcohol. In both cases, this presence of alcohol is favourable since it tends to limit the microbial contamination of the must and of the sugary liquor. Microbial contamination is in fact a problem frequently encountered industrially, and the presence of alcohol can prevent having to use antimicrobial treatments, notably by adding antibiotics or other compounds.

Advantageously, the biomass is pretreated beforehand by impregnation with an acidic, basic or oxidizing aqueous solution, then cooking or steam explosion. This is a known pretreatment, an example of which is described in patent EP 3 728 408.

Preferably, the extraction of the sugars is carried out on a pretreated biomass which has an insoluble solids (ISS) content of at least 20%, notably of at least 25% or of at least 30%, and preferably of at most 70% or 65%, notably of between 25% and 65%.

The insoluble solids ISS content can be determined in the following way: the sample is vacuum filtered by performing successive rinses with deionized water with a mass ratio between 40 and 100, then the sample is dried at 105° C. until a constant mass is obtained. The mass lost during the washing, the filtration and the drawing corresponds to the mass of water (of liquid) initially present in the sample and also to the soluble materials contained in the liquid fraction; the remaining mass corresponds to the insoluble solids ISS.

Preferably, the extraction of the sugars is carried out on a pretreated biomass which has a solids content SC of at least 25%, notably of at least 30% or of at least 35%, and preferably of at most 70% or 65%, notably of between 30% and 65%.

The solids content, SC, is determined according to Standard ASTM E1756-01 which consists in measuring the loss of mass of the liquid fraction by drying at 105° C. until a constant residue mass is obtained. The mass lost during the drying corresponds to the mass of water (of liquid) initially present in the sample, and the remaining mass corresponds to the solid and soluble materials contained in the liquid fraction.

According to one variant, it is possible to provide for the extraction of the sugars by a step of adjustment of the solids content SC of the pretreated biomass, notably by a prior solid/liquid separation operation, preferably of the filtration or centrifugation type.

Preferably, the extraction of the sugars from the pretreated biomass according to the invention comprises contacting said pretreated biomass with the alcoholic or aqueous-alcoholic extraction solution, notably suspending in said solution, then solid/liquid separation.

Optionally, the extraction of the sugars according to the invention can comprise, after the solid/liquid separation, washing of the solid phase obtained by said separation, with an alcoholic or aqueous-alcoholic washing solution. The washing is then preferably performed continuously, in cocurrent or countercurrent mode.

The extraction solution and the washing solution, when washing is provided for, can have the same composition, with the same alcohol(s), or can have one or more different alcohols. In the case of aqueous-alcoholic solutions, the alcohol contents thereof relative to the water may also be identical or different. Thus, in the case where the extraction of the sugars and the washing of the solid phase obtained at the end of the solid/liquid separation is performed in stages, various proportions of alcohol can be used. It is also possible to carry out a final washing of the solid phase with an aqueous solution not containing alcohol.

In the context of the present invention, when a solid/liquid separation is carried out, the "solid phase" separated should be understood as containing the solid phase itself and the liquid phase trapped in said solid phase.

The contacting of the pretreated biomass with the alcoholic or aqueous-alcoholic solution can be performed using a mixer continuously (as described in patent EP 3 587 583 mentioned above) or batchwise, in one or more steps/stages.

The solid/liquid separation can be performed batchwise or continuously, notably using a filter press or a belt filter (as described in patent EP 3 587 583 mentioned above). Advantageously, the extraction solution and/or the washing solution, when washing is provided for, comprises at least one alcohol chosen from: methanol, ethanol, isopropanol, n-butanol and isobutanol. The preferred alcohol is ethanol.

Preferably, the extraction solution and/or the washing solution, when washing is provided for, is an aqueous-alcoholic solution containing at least 5% by weight of alcohol, notably at least 10% by weight, preferably between 5% by weight and 96% by weight, or between 10% by weight and 85% by weight, or between 15% by weight and 50% or 70% by weight of alcohol. Having this proportion of alcohol in water gives a solution which provides the desired effect without reaching a level of alcohol consumption that is too high and that would not be economically advantageous.

Very preferably, the alcohol content is between 15% and 50% by weight, so as to increase the flashpoint of the aqueous-alcoholic solution in order to dispense with certain industrial constraints, and to limit the losses of alcohol by evaporation. It should also be noted that an aqueous-alcoholic solution is easier to handle and to store in an industrial facility than pure alcohol.

In actual fact, the choice of the proportion of alcohol in the extraction solution (and/or washing solution when there is washing) depends notably on the water content in the pretreated biomass before extraction, which can vary to a large extent from one type of biomass to another. (In order to stabilize/modify this content, the invention can, as already indicated above, adjust the solids content SC of the pretreated biomass before extraction.)

One solution consists in adjusting the alcohol content of the aqueous-alcoholic extraction solution, and also the ratio of the mass flow rate of said solution to the mass flow rate of biomass, so that the alcohol content in the liquor obtained is at most 70% by weight solute excluded, preferably at most 50% by weight solute excluded, and preferably at least 10% by weight solute excluded.

It is possible to adjust the content of alcohol (alcohol/water+alcohol) in the extraction solution as a function of the content of alcohol desired (alcohol/water+alcohol), sugars excluded, in the liquor obtained.

It is possible to select operating parameters for the step of contacting the pretreated biomass and the extraction solution so that, in the end, the desired ISS content for carrying out the separation and then the optional washing, notably as a function of the type of equipment chosen to carry out the separation, and the desired target efficiency of separation are obtained.

Preferably, the extraction according to the invention is carried out at moderate temperature, less than or equal to 100° C., notably less than or equal to 80° C., notably less than 80° C., and for example of at least 10° C., notably between 15 and 75° C. or between 20 and 60° C. In fact, it can be carried out at ambient temperature (therefore for example between 10 and 20-25° C.).

Preferably, the contacting of the pretreated biomass (and/or the washing when it is provided for) is carried out at moderate temperature, and even at ambient temperature, notably at a temperature of less than or equal to 100° C., notably between 10 and 80° C., preferably between 20 and 60° C. The temperature in question is understood to be the temperature of the mixture in the step of contacting the biomass with an alcoholic or aqueous-alcoholic solution. Preferably in this configuration, the adjusting of the temperature of the mixture is carried out by adjusting mainly the temperature of the alcoholic or aqueous-alcoholic extraction solution. (The temperature is understood to be the temperature of the alcoholic or aqueous-alcoholic washing solution in the washing step if it is provided for.)

The liquor obtained can be treated in various ways in order to upgrade the sugars extracted:
 the free sugars of the liquor can be converted to furfural, notably by acid catalysis dehydration,
 or the free sugars of the liquor can be converted to xylitol and/or sorbitol, notably by metal catalysis hydrogenation,
 or else they can be converted to alcohol, notably by alcoholic fermentation.

The liquor obtained can be treated in order to deplete it in mineral salts, notably by liming and/or by bringing into contact with one or more active substrate(s) such as ion-exchange resin(s) and/or by electrodialysis.

Optionally, the liquor can be treated with other substrates, of active carbon type for example, in order to deplete it in other compounds, the active carbon thus being capable of capturing coloured compounds contained in the liquor.

Advantageously, the free-sugar liquors can therefore be treated by liming. A liming operation consists in adding, to the liquor of extracted free sugars, a solution of quicklime water, that is to say a saturated aqueous solution of calcium hydroxide $Ca(OH)_2$. The concentration of the limewater solution added is between 5% and 40% by weight, notably between 10% and 20% by weight. The mixing of the limewater and the sugar liquor is carried out at a temperature of between 20 and 80° C. The pH of the mixture obtained is between 8 and 11.5, preferably between 9 and 10.5. The hydroxyl anions $HO^-$ allow the neutralization of the acidic pH induced by the protons H+, and induce the formation of water. The calcium cations $Ca_2^+$ induce partial precipitation of the sulfate ions $SO_4^{2-}$, in the form of calcium sulfate. The precipitate formed can be removed by filtration, decanting or centrifugation. The liming operation can also make it possible to remove various contaminants, mainly inorganic contaminants, but also organic contaminants.

The liming on a sugar liquor produced according to the invention, that is to say an aqueous-alcoholic solution of sugars, is much more effective than liming on an aqueous solution of sugars. Nevertheless, it does not always make it possible to reduce the concentration of salts to very low contents. In this case, the liming can be added to or replaced with an operation aimed at further/totally eliminating the mineral salts, notably in the case where it is intended to subsequently concentrate the sugar liquor.

For very effective elimination of the salts, an ion exchange resin can be used: the liquor (optionally pre-limed) can be passed through anion exchange resins in hydroxide form, and then through cation exchange resins in protonated form. The anions and the cations present in the aqueous solution of free sugars are retained on the anion and cation exchange resins, respectively, and release hydroxide anions and protons respectively. Said hydroxide anions and protons react together in totality so as to form water. The saturated resins can then be regenerated.

It is also possible to use the electrodialysis technique, which operates on the same principle as ion exchange resins, but the ion exchange takes place through selective membranes, under the effect of an electric current producing the hydroxide anions and the protons required.

When an ion exchange resin and/or electrodialysis is used on a solution of sugary liquor produced by the present invention, it can be carried out on the solution produced by the invention, on the solution produced by the invention that has undergone pre-liming, or on the solution produced by the invention from which the solvent (ethanol, etc.) has been removed by evaporation and/or distillation, optionally in addition to liming.

It is also possible to concentrate the liquor obtained with respect to the sugars, notably by evaporation, optionally after and/or before a treatment for depleting said liquor in mineral salts. The step of concentrating the sugar liquor produced by the present invention can be carried out according to any technique known to those skilled in the art, for example by multiple effect evaporation or with mechanical steam compression.

The concentrating can be carried out with recovery of the alcohol and/all the water in order to constitute all or part of the alcohol and/or of the water of the alcoholic or aqueous-alcoholic extraction solution used and/or for the washing solution when washing is provided for. The concentrating of the liquor can be carried out by evaporation and alcohol and/or water can then be recovered in order to constitute all or part of the alcohol or of the aqueous-alcoholic solution required for carrying out the invention (extraction and/or optional washing): the constituent(s) of the alcoholic or aqueous-alcoholic solution can thus be at least partially recycled. The condensates obtained after concentration of the sugar liquor according to the invention, mainly consisting of alcohol and water, can be distilled in a distillation column in order to separate all or part of the alcohol from the water.

According to one embodiment, the liquor obtained can be treated in order to deplete it in mineral salts (at high concentrations under hot conditions), then it can be concentrated, and then finally a (cold) crystallization can be carried out on this liquor depleted in mineral salts and concentrated with respect to sugars.

A subject of the invention is also a process as described above and which comprises an enzymatic hydrolysis of the must obtained after extraction, which is followed by, or is concomitant with, an alcoholic fermentation, then a distillation of the liquid fraction obtained after fermentation. Thus, a part of the alcohol and/or all or part of the water recovered during the distillation can be used to constitute all or part of the alcoholic or aqueous-alcoholic extraction solution (and/or of the washing solution when washing is provided for).

A subject of the invention is also a process for treating a lignocellulosic biomass which comprises the following successive steps:
impregnation of the biomass with an acidic, basic or oxidizing aqueous solution, in order to obtain an impregnated biomass,
pretreatment of the impregnated biomass by cooking or steam explosion, in order to obtain a pretreated biomass,
enzymatic hydrolysis of the pretreated biomass, in order to obtain a hydrolysed biomass,
optionally, alcoholic fermentation of the hydrolysed biomass,
and such that an extraction of the free sugars is carried out, using an alcoholic or aqueous-alcoholic extraction solution, on all or part of the pretreated biomass before the enzymatic hydrolysis thereof.

According to the invention, it is thus possible to anticipate performing the extraction of the sugars on an entire pretreated biomass, or only on a part thereof.

In the latter situation, provision is preferably made for all of the part of the pretreated biomass having undergone the extraction of the sugars and of the part which has not undergone said extraction to be treated by enzymatic hydrolysis.

The extraction of the free sugars according to the invention can comprise at least partial recycling of a liquid phase extracted from the filter-type device performing the solid/liquid separation to the inlet of the mixer-type device performing the contacting. This recycling makes it possible to reduce the consumption of alcoholic or aqueous-alcoholic solution, and has proved, surprisingly, to enable both a more efficient mixing in the mixer and an extraction of liquid phase(s) at the filter that is (are) more concentrated with respect to sugars.

These various possible recycling operations make it possible to reduce the alcohol and water consumption of the washing process, and/or to reduce energy consumptions. They can be carried out individually or in addition to one another. Thermal integration between the various optional steps is possible, and even recommended.

In terms of pressure conditions used during the extraction: the operating pressure depends on the step in question (contacting, solid/liquid separation and optional washing), on the technology retained and on the point of measurement. In many technologies, the pressure is the driving element which makes it possible to circulate the liquid phase enabling the extraction and/or the washing. In general, the technologies all have a fluid at atmospheric pressure and a pressure differential between 0.2 and 25 bar between the ingoing and outgoing fluids, and even more preferably between 0.4 and 20 bar. This pressure differential may be negative during the solid/liquid separation. This pressure differential may also be obtained by applying an external pressure to the solid/liquid mixture, as in the case of a belt press, or during the use of a press as an option on a belt filter.

For example, in the case of the use of a filter press for the solid/liquid separation, the fluid extracted from the filter is at atmospheric pressure and the ingoing fluid is at a higher pressure. This pressure is variable as a function of the operating phase. During the filtration, the pressure of the fluid to be filtered increases between atmospheric pressure and a maximum pressure which is dependent on the equipment, generally between 5 and 15 bar. During the optional washing step, the pressure of the washing fluid is constant, and generally greater than the pressure at the end of filtration and generally is between 6 and 20 bar.

Likewise for example, during the use of a belt filter for the solid/liquid separation, the mixture is deposited on the filter and a pressure reduction is applied under the filter: the liquid is thus drawn from the "cake" deposited on the filter and passes through the filter before being collected in containers. The pressure reduction applied is generally between 0.2 and 2 bar, preferentially between 0.4 and 1 bar. The operation is sequential; the belt moves according to a defined time sequence; during the movement of the belt, there is no pressure reduction applied. Optionally, a press may be added in order to increase the pressure applied on the mixture deposited on the belt and to increase the extraction of liquid.

DESCRIPTION OF THE EMBODIMENTS

The invention will be described in detail below with the help of non-limiting examples illustrated by FIGS. 1, 2 and 3. The same references correspond to the same components/fluids/products on all of the figures. The figures are extremely diagrammatic.

It has been discovered, with the present invention, that it is possible and very advantageous to carry out an extraction of the free sugars from the pretreated biomass with an alcohol or an aqueous-alcoholic mixture. Preferably, the alcohol used is ethanol, which at first glance appears to be a choice that goes against the desired aim, which is to extract the free sugars from the biomass, since ethanol is rather a poor solvent for sugars (sugar solubility less than 1 wt %). Ethanol is known to be an "anti-solvent" for sugars, used for facilitating their crystallization.

Advantageously, the alcohol or the aqueous-alcoholic mixture used for the extraction of the free sugars can be produced by a step of fermentation of all or part of the free sugars recovered in the pretreated biomass washing step.

Advantageously, the alcohol or the aqueous-alcoholic mixture used for the extraction of the free sugars from the pretreated biomass can be produced by enzymatic hydrolysis and fermentation of the extracted pretreated biomass, called washed must.

It is thus possible to integrate the process for extraction of the free sugars into the complete biomass conversion process in an industrial facility for producing ethanol, or for producing ethanol and sugars.

The use of an alcohol or an aqueous-alcoholic mixture for extracting the free sugars from the biomass makes it possible to obtain free-sugar extraction yields that are at least equivalent to the use of water as solvent, all things being otherwise equal (flow rates, performance and operating mode of the liquid-solid separation tool).

On the other hand, the use of an alcohol or of an aqueous-alcoholic mixture for extracting the free sugars from the biomass makes it possible to obtain additional advantages compared to a purely aqueous washing solution: reduction of the energy consumption associated with concentrating the extracted free sugars in the liquor; reduction in the costs associated with removing the salts; limitation of the risks of microbial contaminations of the washed must and of the solution of free sugars extracted from the biomass.

Preferably, the ratio of mass of alcoholic or aqueous-alcoholic solution to the mass of biomass (on an insoluble solids basis) used in the present invention is between 0.1 and 100. Preferably, the ratio of mass of alcoholic or aqueous-alcoholic solution to the mass of biomass is between 1 and 10. The mass ratio can be produced on the basis of the ratio of the mass flow rates when the operation is a continuous feed operation, or on the basis of the ratio of the masses involved on a cycle when the operation is a batchwise operation.

The biomass produced in the pretreatment step contains an amount of water which can be variable, depending on the type and the conditions of the pretreatment. The extraction of the free sugars can comprise a step of bringing into contact with an alcoholic or aqueous-alcoholic solution. The extraction of the free sugars comprises at least one liquid-solid separation step. The extraction of the free sugars can comprise a step of washing the solid obtained after separation of the solid/liquid mixture, using an alcoholic or aqueous-alcoholic solution.

Preferably, the alcohol content in the aqueous-alcoholic solution and the ratio of mass of aqueous-alcoholic solution to the mass of biomass can be adjusted so that the alcohol content in the liquor of extracted free sugars is less than 70% by weight (solute excluded), preferably less than 50% by weight (solute excluded).

Preferably, the alcohol content in the aqueous-alcoholic solution and the ratio of mass of aqueous-alcoholic solution to the mass of pretreated biomass can be adjusted so that the alcohol content in the liquor of extracted free sugars is greater than 10% by weight (solute excluded).

The operation for washing the solid obtained after optionally bringing the pretreated biomass into contact with an alcoholic or aqueous-alcoholic solution and after liquid-solid separation is carried out at a pressure which depends on the technology selected, preferably with a pressure differential between the input of the washing solution and the output of the sugary liquor of between 0.2 and 25 bar, and preferentially between 0.4 and 20 bar. Preferably, at least one input or at least one output of liquid is, depending on choice, at atmospheric pressure.

The operation for extraction of the free sugars from the biomass can be carried out by any liquid-solid extraction techniques known to those skilled in the art. This liquid-solid extraction can be carried out in one or more contact stages. If several contact stages are implemented, the aqueous-alcoholic solution(s) can be used in crosscurrent mode, in cocurrent mode or in countercurrent mode with respect to the biomass.

The operation for extraction of the free sugars may be batchwise or continuous. In the case of a crosscurrent operation, the aqueous-alcoholic solutions successively brought into contact with the biomass can have different alcohol contents.

In a non-limiting manner, the extraction of the free sugars can be carried out by a prior dispersion of the biomass in an aqueous-alcoholic solution, then a liquid-solid separation by means of equipment such as a filter press or a belt filter.

Advantageously, the aqueous-alcoholic solution is produced on site, by fermentation of a fraction of the sugars of the lignocellulosic biomass in alcohol.

In one embodiment, the pretreated biomass from which its free sugars have been removed by the process according to the invention, called washed must, can then be treated in a hydrolysis and fermentation step for the purpose of producing ethanol. In a non-limiting manner, the must obtained at the end of fermentation, containing approximately between 4% by weight and 10% by weight of ethanol, can be filtered in order to remove the residual solid from it, and then can be used as it is for carrying out the invention. In a non-limiting manner, the must obtained at the end of fermentation, containing approximately between 4% by weight and 10% by weight of ethanol, can be filtered in order to remove from it the biomass and the lignin or any other residual solid, and then distilled according to any technique known to those skilled in the art, in a distillation column or beer column. A water-ethanol mixture having an alcohol content of between 10% by weight and 96% by weight, and which can be used to reconstitute an aqueous-alcoholic solution required for carrying out the invention, can be obtained by means of a side draw-off from the column.

In one embodiment, a fraction of the free sugars present in the liquor obtained by carrying out the invention is subjected to a treatment (pH adjustment notably) in such a way that it can be treated by alcoholic fermentation. By way of illustration, this fermentation may be an ethanolic fermentation (in the presence of yeast) or a fermentation in an acetone/butanol/ethanol mixture or else a fermentation in an isopropanol/butanol/ethanol mixture. The fermentation must can be distilled in order to recover solutions of water and of alcohol(s) or of water+alcohol mixtures, which can be used to carry out the invention.

The invention can apply to any type of pretreated lignocellulosic biomass, for example originating from biomass such as forestry residues, short-rotation coppice, Miscanthus, agricultural residues, such as cereal residues of (wheat) straw type or maize residues. Before pretreatment, the biomass may, in a known manner, be conditioned with notably a mechanical treatment (milling) so as to obtain biomass particles preferably having a size of at most 300 mm. Generally, the conditioned biomass has a particle size (the largest size) of at most 300 mm, most often of at least 1 mm, and often of between 2 and 200 mm.

A non-limiting example of implementation of the invention consists in carrying out:

a—an explosive pretreatment step, such as for example a steam explosion pretreatment of the lignocellulosic biomass after impregnation thereof with an acidic solution;

b—a step of extraction of the free sugars from the pretreated biomass obtained in step a—, by means of an aqueous-alcoholic solution, the pretreated biomass being brought into contact with the aqueous-alcohol solution, a solid/liquid separation and, optionally, washing of the solid with the aqueous-alcoholic solution, in order to recover, in a liquor, the sugars released by the biomass during the pretreatment thereof and a (washed) must;

c—a step of valorizing of the sugars of the liquor recovered in step b—;

d—an optional step of valorizing of the (washed) must obtained in step b—.

A non-limiting example of implementation of step c) consists in carrying out:

c1—a liming step
c2—a first concentration step
c3—a step of demineralization using resin or electrodialysis
c4—a second concentration step
c5—a crystallization step.

A non-limiting example of implementation of step d— consists in carrying out:

d1—a step of dissolving the (washed) must
d2—an enzymatic hydrolysis of the cellulosic fraction of the must
d3—a step of ethanolic fermentation of the sugars released by step d2—, optionally coupled to d2—
d4—a step of distillation of the fermentation must, making it possible to produce ethanol, water, and the aqueous-alcoholic solution required for implementing step b—.

DESCRIPTION OF THE FIGURES

Figure 1:
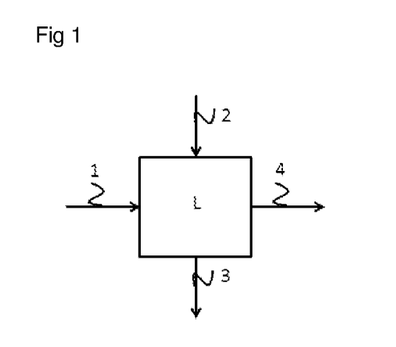
FIG. 1 is a block diagram of a sugar extraction operation according to a first embodiment of the invention.

With reference to FIG. 1, a pretreated biomass 1 obtained by pretreatment of the lignocellulosic biomass undergoes an operation of extracting the free sugars L with an aqueous-alcoholic solution 2 of water-ethanol type. It produces a washed must 4 and a liquor 3 composed of an aqueous-alcoholic solution of extracted free sugars.

Figure 2:
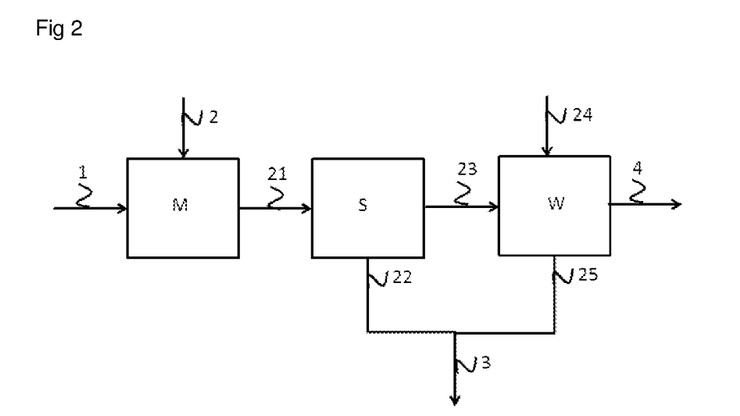
FIG. 2 is a block diagram of a sugar extraction operation according to a second embodiment of the invention.

FIG. 2 represents an extraction of the sugars according to the invention, which comprises an operation of bringing the pretreated biomass into contact with an alcoholic or aqueous-alcoholic solution, then a solid/liquid separation, and washing of the solid-phase obtained after separation, with an alcoholic or aqueous-alcoholic washing solution. With reference to FIG. 2, a pretreated biomass 1 obtained by pretreatment of the lignocellulosic biomass is brought into contact, in a mixer M, with an aqueous-alcoholic solution 2 of water-ethanol type. The solid/liquid mixture 21 then undergoes a solid/liquid separation S. It produces a liquid phase 22 composed of an aqueous-alcoholic solution of extracted free sugars, and a solid phase 23 depleted in free sugars.

The solid phase 23 undergoes a washing operation W with an aqueous-alcoholic solution 24 so as to produce a washed must 4 which is more depleted in free sugars than the solid phase 23, and a washing filtrate 25 composed of an aqueous-alcoholic solution of free sugars. This solution 24 can have the same composition as the extraction solution 2, or can have a different composition.

The liquid phase 22 obtained by solid/liquid separation and the washing filtrate 25 can be mixed so as to constitute the liquor 3 of free sugars in an aqueous-alcoholic solution.

The succession of the contacting, solid/liquid separation and washing steps makes it possible to increase the recovery of the free sugars in the liquor.

It should be noted that the invention can provide for operations for recycling fluids, notably, for example, the solution 25, in order to add to or replace the extraction solution 2.

Figure 3:
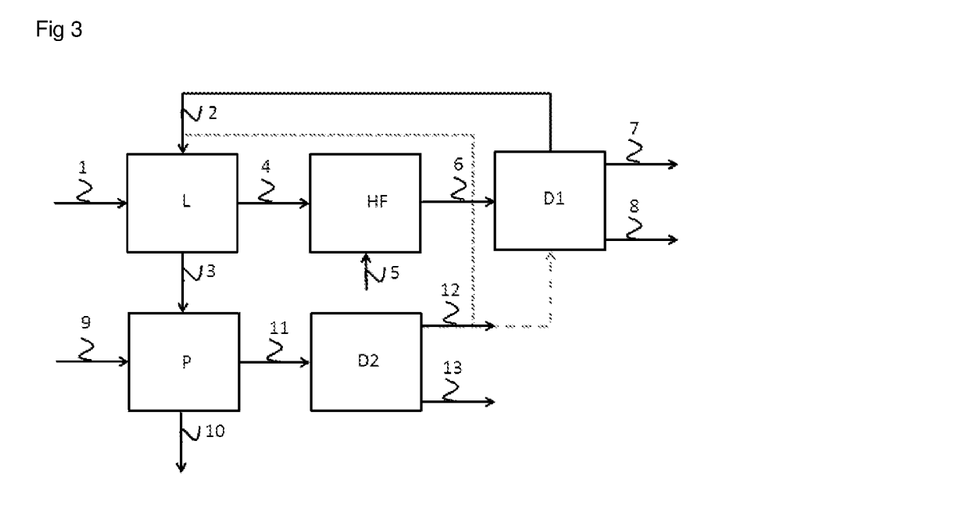
FIG. 3 is a block diagram of a sugar extraction operation according to a third embodiment of the invention.

With reference to FIG. 3, a biomass obtained by pretreatment of the lignocellulosic biomass 1 undergoes an operation of extracting the free sugars L with an aqueous-alcoholic solution 2 of ethanol+water type. It produces a washed must 4 and an aqueous-ethanolic solution of extracted free sugars: the liquor 3. The operation for extraction of the free sugars L comprises bringing the pretreated biomass 1 into contact with the water-ethanol mixture 2, then a solid/liquid separation and optionally a step of washing (as with the stream 24 of FIG. 2) the solid phase obtained by the separation, with the water-ethanol mixture 2.

It should be noted that the extraction L can be carried out in one step as in FIG. 1 or in several steps as in FIG. 2.

The washed must 4 then undergoes an enzymatic hydrolysis operation HF and an alcoholic fermentation operation, which are dissociated/successive or simultaneous, with the aim of producing an aqueous solution of ethanol 6. To this end, the washed must is brought into contact with one or more aqueous solutions 5 containing the enzymes and the yeasts required for this transformation. The aqueous solution of ethanol 6 thus produced then undergoes a distillation operation D1 to produce ethanol 7 and vinasses 8. The ethanol stream 7, in a known manner, is not necessarily pure and may still contain water.

An aqueous-alcoholic solution 2 is drawn-off from the distillation column D1 in order to feed the extraction operation L.

The aqueous-ethanolic solution of extracted free sugars (liquor) 3 undergoes one or more optional purification steps, in this case in the form of liming (that is to say depleted in certain mineral salts of the sulfate type). The stream 9 represents the separation agent(s) (calcium hydroxide, resins, etc.) intended to deplete the liquor 3 of its mineral salts, notably of sulfate type, originating from the sulfuric acid used to pretreat the biomass. This stream 9 is brought into contact with the aqueous-ethanolic solution of extracted free sugars 3. The stream 10 represents the separation agent(s) which have captured the mineral salts (calcium sulfate, saturated resins, etc.), which are then replaced or regenerated.

The aqueous-ethanolic solution of purified free sugars (liquor depleted in salts) 11 undergoes an evaporation concentration operation D2 with the aim of producing an aqueous solution of concentrated purified free sugars 13 and an aqueous-alcoholic solution 12. This aqueous-alcoholic solution 12 can advantageously be directly recycled to the step of extraction of the free sugars of the must L (dashed line on the figure), or indirectly recycled by feeding the distillation column D1.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 21/03.229, filed Mar. 30, 2021, are incorporated by reference herein.

EXAMPLES

A lignocellulosic biomass, wheat straw, containing 30% by weight of hemicellulose, the solids content of which is 90% by weight and the insoluble solids content of which is 80% by weight, undergoes a pretreatment which consists of:
- an impregnation with an aqueous solution of sulfuric acid: the impregnation is performed in the presence of acidic liquor heated to 80° C. and a residence time of 2 minutes. The acid concentration in the liquor is 2.5% by weight (expressed as weight % of $H_2SO_4$). The solids content SC of the impregnated biomass is 25% by weight;
- the introduction of this impregnated biomass into a pressurized reactor heated to 180° C. with injection of steam, for a residence time of 5 min, enabling a yield of conversion of the hemicellulose to monomeric xylose of 70% by weight;
- a decompression at atmospheric pressure releasing steam and a pretreated biomass having a solids content of 50% by weight and an insoluble solids content of 40% by weight.

The pretreated biomass thus produced is used to produce Examples 1 and 2 (not in accordance with the invention), and 3 and 4 (in accordance with the invention).

The extraction of the free sugars present in the pretreated biomass, according to the invention and for the four examples, is carried out in two steps.

1/ The pretreated biomass is first repulped, at ambient temperature at a solids content SC of 20% by weight and an insoluble solids ISS content of 16% by weight, with an aqueous solution of a mixture having ethanol contents of between 0 and 70% by weight, in a proportion of 1.3 g of mixture solution per gram of pretreated biomass. The term "repulping" is intended to mean the operation consisting in bringing the pretreated biomass into contact with the aqueous-alcoholic solution by suspending the biomass in the solution.

2/ The repulped biomass feeds a filter press in order to carry out a solid/liquid separation with the production of the sugar liquor and a washed must. The repulped biomass is first filtered under pressure at a temperature of 50° C., then the solid phase retained by the filtering cloth in the filtration chambers of the filter press is compacted by injecting air for pressing. The insoluble solids content in the washed must after liquid-solid separation is approximately 45% by weight for the various examples. The sugar content in the various liquors is determined by HPLC (high-performance liquid chromatography), and makes it possible to determine a sugar extraction yield, defined as being the ratio between the amount of extracted sugars in the liquor and the amount of sugars present in the pretreated biomass, of about 75% for all the examples. The content of sugars (notably glucose and xylose) in the liquor obtained is 56 g/kg. The $H_2SO_4$ in the liquor obtained is about 1.1% by weight determined by ion chromatography. Optionally, the solid phase retained by the filtering cloth in the filtration chambers of the filter press before compacting is washed with the aqueous-alcoholic solution. This washing produces a washing filtrate. This optional washing step takes place at constant washing solution flow rate. The pressure is slightly lower than the filtration pressure. The sugar liquors are then limed at 50° C., in the following way to reach a pH of 10: The concentration of the limewater solution added is equal to 15% by weight. The mixture of the limewater and the liquor is left to stir for 30 to 60 minutes. Once the limewater is mixed with the sugar liquor, the lime immediately reacts with the non-sugary components by virtue of the presence of calcium ions and hydroxide ions Calcium ions help to dissociate certain organic acids by forming calcium salts which precipitate: oxalic, citric, tartaric, phosphoric acid salts. The calcium also induces reactions which coagulate colouring compounds. The hydroxide ions neutralize the acids and result in the precipitation of magnesium hydroxide or iron oxides. The ion concentration is determined by ion chromatography, before and after liming, for the various examples. It makes it possible to determine a degree of elimination of sulfate ions, which is given in Table 1 below. A 10% loss of sugars is noted after liming.

The sugar liquors are then concentrated using a rotary evaporator operating under vacuum, to a concentration level of approximately 300 g sugars/kg water.

Moreover, a gas chromatography analysis is carried out to determine the ethanol content (and by difference the water content) in the solvent evaporated off. On this basis, the enthalpy of vaporization corresponding to the energy to be introduced in order to concentrate the sugars is calculated, relative to the reference case (that is stay in the absence of ethanol in the extraction solution) which is Example 1. The energy gains are reported in the table below.

TABLE 1

| Example | wt % Ethanol in the extraction solution | wt % Ethanol in the liquor before liming and evaporation | Degree of elimination of sulfates (%) | Concentration to 300 g/kg water | Reduction in enthalpy of vaporization (%) relative to Example 1 |
|---|---|---|---|---|---|
| 1 | 0 | 0 | 86.4 | Precipitation of salts | 0.0 |
| 2 | 15 | 10 | 95.9 | Precipitation of salts | 11.3 |
| 3 | 30 | 20 | 98.2 | — | 22.6 |
| 4 | 50 | 33 | 99.7 | — | 37.7 |
| 5 | 70 | 47 | 99.9 | — | 52.8 |

For Comparative Examples 1 and 2, where the degrees of elimination of the salts are lower, a precipitation of the salts, which is not desirable (soiling of the equipment), is observed.

It is seen that this precipitation correlates with the ethanol content in the liquor, which itself correlates with the ethanol content of the extraction solution and characteristics of the biomass used here (its initial water content before extraction). The preferred minimum value of ethanol in the liquor is here at least 15% by weight, preferably at least 18% or 20% by weight, which amounts to choosing preferably an ethanol content in the extraction solution of greater than 15% by weight, notably of at least 18% or of at least 20% or of at least 25% by weight.

It should be noted that, depending on the implementation of the extraction, notably depending on the choice of the composition (of the alcohol(s)) of the extraction solution and depending on the nature of the biomass, the minimum alcohol content of the extraction solution may be less than or equal to 15% by weight, for example between 5% and 15% or between 5% and 10% by weight, and can already bring a positive effect according to the invention (energy gain and little/no soiling by salt precipitation). The invention provides a gain, depending on the case, as long as the extraction solution comprises a not insignificant alcohol content, notably of at least 5% by weight.

From these results, it is noted that Examples 3 to 5, according to the invention, with repulping of the pretreated biomass with an aqueous-alcoholic solution allow, at similar sugar extraction yield in the liquor (extraction yield of 75.6% by weight for the examples according to the invention) a much more efficient treatment of depletion of mineral salts of the liquor, by going to a sulfate elimination of more than 95% and even more than 98%, which is noteworthy.

In addition, a large reduction in the enthalpy of vaporization, which is all the greater the larger the alcohol content of the extraction solution, and which results in a decrease in the energy cost of the extraction, is noted, the evaporation of a water-alcohol mixture having a lower consumption than the evaporation of an entirely aqueous phase. A favourable impact on equipment costs can also be anticipated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for treating a lignocellulosic biomass comprising:
    pretreating the biomass by impregnation with an acidic, basic, or oxidizing aqueous solution, and then subjecting the biomass to steam explosion, to form a pretreated biomass in the form of a solid/liquid mixture, and
    extracting free sugars from said pretreated biomass by contacting the pretreated biomass in the form of a solid/liquid mixture with an aqueous-alcoholic extraction solution having an alcohol content of between 15% and 70% by weight, and then subjecting the mixture of pretreated biomass and extraction solution to solid/liquid separation so as to obtain a liquid phase enriched in free sugars, called liquor, and a solid phase depleted in free sugars, called must, wherein extraction is carried out at a temperature of less than or equal to 80° C. and the liquor comprises xylose.

2. The process according to claim 1, wherein the pretreated biomass has a solids content of at least 25%.

3. The process according to claim 1, wherein extraction of the free sugars from the pretreated biomass comprises contacting said pretreated biomass with the aqueous-alcoholic extraction solution, then solid/liquid separation.

4. The process according to claim 3, wherein extraction of the free sugars further comprises, after solid/liquid separation, washing the solid phase obtained by said separation with an alcoholic or aqueous-alcoholic washing solution.

5. The process according to claim 3, wherein contacting of the pretreated biomass (1) with the aqueous-alcoholic extraction solution is performed, continuously or batchwise, using a mixer in one or more steps/stages.

6. The process according to claim 3, wherein the solid/liquid separation is performed batchwise.

7. The process according claim 1, wherein the extraction solution comprises at least one alcohol selected from: methanol, ethanol, isopropanol, n-butanol, and isobutanol.

8. The process according to claim 1, wherein the aqueous-alcoholic extraction solution has an alcohol content of between 15% and 50% by weight of alcohol.

9. The process according claim 1, wherein the alcohol content of the aqueous-alcoholic extraction solution and the ratio of mass flow rate of said aqueous-alcoholic solution to mass flow rate of pretreated biomass are adjusted so that the alcohol content in the liquor is at most 70% by weight solute excluded.

10. The process according to claim 1, wherein the liquor obtained is treated to deplete mineral salts.

11. The process according to claim 1, wherein the liquor (3) obtained is concentrated with respect to the sugars, after, before, or both before and after a treatment for depleting said liquor in mineral salts.

12. The process according to claim 11, wherein concentrating of the liquor is carried out by evaporation, with recovery of alcohol, water, or both, in order to constitute all or part of the alcohol, the water, or both, of the aqueous-alcoholic extraction solution used for the washing solution when washing is provided for.

13. The process according to claim 1, wherein the process further comprises an enzymatic hydrolysis of the must obtained after extraction, which is followed by, or is concomitant with, an alcoholic fermentation, distillation of a liquid fraction obtained after said fermentation, and in that a part of the alcohol, all or part of the water, or both part of the alcohol and all or part of the water, recovered during the distillation is (are) used to constitute all or part of the aqueous-alcoholic extraction solution.

14. A process for treating a lignocellulosic biomass, said process comprising the following successive steps:
    impregnating the biomass with an acidic, basic, or oxidizing aqueous solution to obtain an impregnated biomass,
    pretreating the impregnated biomass by steam explosion to obtain a pretreated biomass in the form of a solid/liquid mixture,
    subjecting the pretreated biomass to enzymatic hydrolysis to obtain a hydrolyzed biomass, and
    optionally, subjecting the hydrolyzed biomass to alcoholic fermentation,
    wherein an extraction of free sugars from at least a part of pretreated biomass is carried out before subjecting the pretreated biomass to enzymatic hydrolysis, wherein the extraction of the free sugars comprises contacting said pretreated biomass in the form of a solid/liquid mixture with an aqueous-alcoholic extraction solution having an alcohol content of between 15% and 70% by weight at a temperature of less than or equal to 80° C., wherein with the aqueous-alcoholic extraction solution, followed by a solid/liquid separation.

15. The process according to claim 1, wherein extraction is carried out at a temperature of less than 80° C.

16. The process according to claim 1, wherein the pretreated biomass has a solids content of between 30% and 65%.

17. The process according claim 4, wherein the washing solution comprises at least one alcohol selected from: methanol, ethanol, isopropanol, n-butanol, and isobutanol.

18. The process according to claim 4, wherein the washing solution is an aqueous-alcoholic solution containing at least 5% by weight of alcohol.

19. The process according to claim 3, wherein the solid/liquid separation is continuously.

20. The process according to claim 3, wherein the solid/liquid separation is performed using a filter press or a belt filter.

21. The process according to claim 1, wherein extraction is carried out using an aqueous-alcoholic extraction solution having an alcohol content of at least 20% weight.

22. The process according to claim 1, wherein extraction is carried out at a temperature of between 20° C. and 60° C.

23. The process according to claim 1, wherein extraction is carried out by suspending said pretreated biomass in said aqueous-alcoholic extraction solution.

* * * * *